(12) United States Patent
Tsutsumi (10) Patent No.: US 8,226,547 B2
(45) Date of Patent: Jul. 24, 2012

(54) ENDOSCOPE

(75) Inventor: Takuroh Tsutsumi, Aizuwakamatsu (JP)

(73) Assignee: Olympus Medical Systems Corp., Tokyo (JP)

( * ) Notice: Subject to any disclaimer, the term of this patent is extended or adjusted under 35 U.S.C. 154(b) by 917 days.

(21) Appl. No.: 12/246,872

(22) Filed: Oct. 7, 2008

(65) Prior Publication Data

US 2009/0093680 A1    Apr. 9, 2009

(30) Foreign Application Priority Data

Oct. 9, 2007 (JP) .................................. 2007-263728

(51) Int. Cl.
A61B 1/00 (2006.01)

(52) U.S. Cl. ......... 600/140; 600/127; 600/129; 600/139

(58) Field of Classification Search .................. 600/127, 600/129
See application file for complete search history.

(56) References Cited

U.S. PATENT DOCUMENTS

| | | | |
|---|---|---|---|
| 4,085,742 A * | 4/1978 | Okada | 600/112 |
| 4,347,837 A * | 9/1982 | Hosono | 600/139 |
| 4,807,598 A * | 2/1989 | Hasegawa | 600/140 |
| 4,841,952 A * | 6/1989 | Sato et al. | 600/129 |
| 4,879,991 A * | 11/1989 | Ogiu | 600/129 |
| 5,052,445 A * | 10/1991 | Berchem | 138/155 |
| 5,281,454 A * | 1/1994 | Hanson | 428/36.3 |
| 5,591,120 A * | 1/1997 | Machida et al. | 600/140 |
| 6,447,445 B1 * | 9/2002 | Hirano | 600/129 |
| 6,514,198 B2 * | 2/2003 | Ishibiki | 600/133 |
| 6,916,285 B2 * | 7/2005 | Takase | 600/133 |
| 7,833,154 B2 * | 11/2010 | Aono et al. | 600/140 |
| 2002/0040179 A1 | 4/2002 | Takahashi et al. | |
| 2003/0158462 A1 | 8/2003 | Takase | |
| 2005/0209508 A1 | 9/2005 | Aono et al. | |
| 2006/0241481 A1 | 10/2006 | Itoi | |

FOREIGN PATENT DOCUMENTS

| | | |
|---|---|---|
| EP | 1 563 784 A1 | 8/2005 |
| EP | 1 707 125 A1 | 10/2006 |
| JP | 6-319677 A | 11/1994 |
| JP | 2001-252242 A | 9/2001 |
| JP | 2007-159854 A | 6/2007 |
| JP | 2008-73186 A | 4/2008 |
| WO | WO 2007/015334 A1 | 2/2007 |

OTHER PUBLICATIONS

Chinese Office Action dated Apr. 2, 2010 with translation.
Japanese Office Action dated Mar. 6, 2012 from corresponding Japanese Patent Application No. JP 2007-263728, together with English language translation.

* cited by examiner

*Primary Examiner* — Matthew J Kasztejna
(74) *Attorney, Agent, or Firm* — Scully, Scott, Murphy & Presser, PC (57) ABSTRACT

An endoscope includes an insertion portion, a resin tubular covering member, a fastening member and a contact surface. The insertion portion includes a bending portion. The resin tubular covering member is covering a covering target part in the insertion portion including the bending portion. The fastening member is wound around the outer periphery of at least one end of the covering member and fastens the end to the covering target part. The contact surface is provided on the side of the covering target part covered with the end, is placed in contact with the end face of the covering member and becomes thinner toward the side of the covering member.

1 Claim, 11 Drawing Sheets

ENDOSCOPE

CROSS-REFERENCE TO RELATED APPLICATIONS

This application is based upon and claims the benefit of priority from prior Japanese Patent Application No. 2007-263728, filed Oct. 9, 2007, the entire contents of which are incorporated herein by reference.

BACKGROUND OF THE INVENTION

1. Field of the Invention

This invention relates to an endoscope having a bending portion covered with a covering member.

2. Description of the Related Art

Figure 15A:
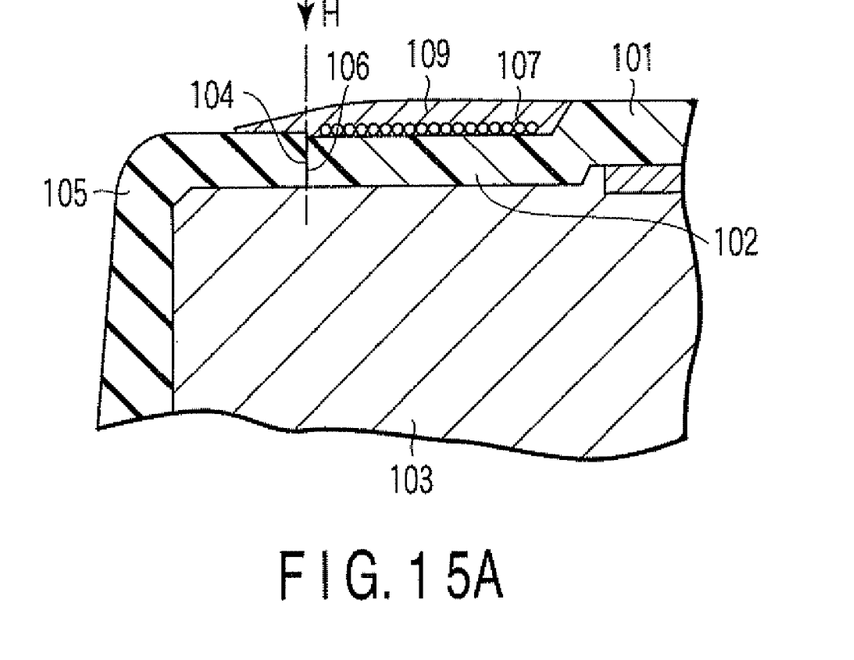
FIG. 15A is a schematic longitudinal sectional view showing a part in the vicinity of the distal portion of a distal hard portion of an insertion portion of an endoscope according to a prior art.

The outer periphery of a bending portion of an endoscope is covered with a flexible covering member called a bending rubber. The bending rubber is formed into a relatively thin tubular shape. The end of the bending rubber is externally wound with a thread such that it is fastened and fixed to members such as a bending tube, a distal hard portion and a joint tube. FIG. 15A shows an example in which a distal end portion 102 of a bending rubber (envelope) 101 is wound with a thread such that it is fixed to a distal hard portion. A distal end 104 of the bending rubber 101 contacts a rear end face (contact surface) 106 of a cover 105 of the distal hard portion. The rear end face 106 of the cover 105 of the distal hard portion is an end face perpendicular to the outer peripheral surface of a main body 103 of the distal hard portion (face orthogonal to the central axis of the distal hard portion), and a step is formed by the rear end face 106 of the cover 105 of the distal hard portion and the outer peripheral surface of the main body 103 of the distal hard portion. Further, the distal end (cut end face) 104 of the bending rubber 101 is put into contact with the rear end face 106.

Endoscopes having such attachment structures are also shown in, for example, US 2002/0040179 A1 and US 2005/0209508 A1. In US 2002/0040179 A1 and US 2005/0209508 A1, a portion wound with a thread to be fixed to the outside of the end of a bending rubber is fitted into an annular concave portion formed smaller in diameter than the outermost periphery of a cover in the outer periphery of the cover of a distal hard portion. The distal end face of the bending rubber is placed in collision with an end face perpendicular to the main body of the distal hard portion located on the distal side of the annular concave portion of the cover.

Figure 16A:
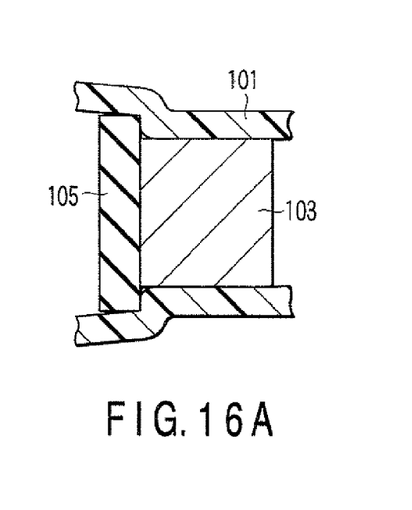
FIGS. 16A to 16D are schematic diagrams sequentially showing the steps of covering the outside of the distal hard portion of the insertion portion of the endoscope according to the prior art with the envelope of the bending portion, and winding a thread around the outside of the main body of the distal hard portion, and then cutting off an extra portion of the envelope.

Furthermore, the operation of covering the bending portion and the distal hard portion with the bending rubber is carried out in the order shown in FIGS. 16A to 16D. First, as shown in FIG. 16A, the bending rubber 101 is brought to cover from the bending portion up to the distal hard portion cover 105 of the distal hard portion main body 103. Here, the inside diameter of the bending rubber 101 in a free state is smaller than the outside diameter of the distal hard portion main body 103. Therefore, the bending rubber 101 covers from the outer periphery of the distal hard portion cover 105 to the outer periphery of the distal hard portion main body 103 in a substantially close contact state.

Figure 16B:
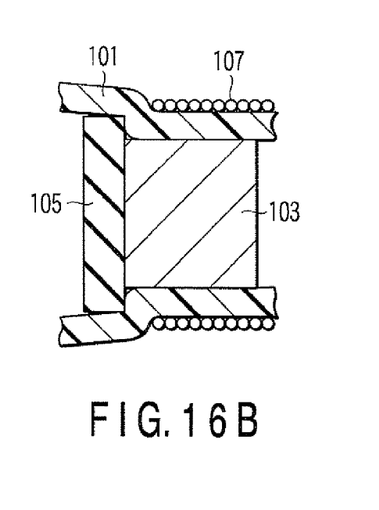

Then, as shown in FIG. 16B, a thread 107 is wound around the outer periphery of the distal end of the bending rubber 101 corresponding to the outer peripheral portion of the distal hard portion main body 103 avoiding the cover 105 of the distal hard portion.

Figure 16C:
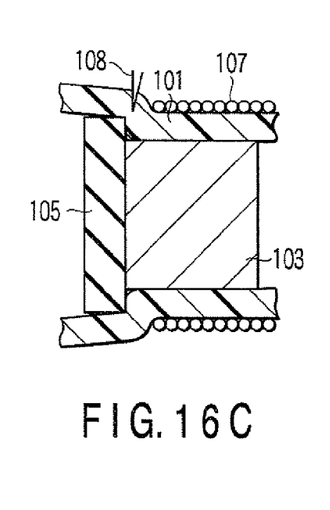

Then, as shown in FIG. 16C, a cutter 108 (e.g., a razor) is put on an extended budging portion located at the step between the rear end of the distal hard portion cover 105 and the distal hard portion main body 103 in the bending rubber 101 fastened by the thread, thereby cutting off an extra portion of the bending rubber 101 covering the outer periphery of the distal hard portion cover 105.

Figure 16D:
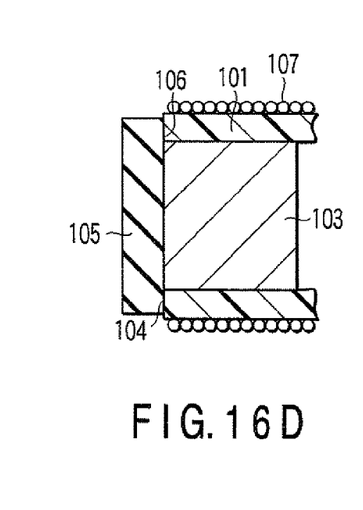

Thus, as shown in FIG. 16D, the distal end of the bending rubber 101 comes into the step, and the distal end 104 of the bending rubber 101 is brought into collision with the rear end face 106 of the cover 105 of the distal hard portion. Subsequently, as shown in FIG. 15A, an adhesive 109 is applied to the outer periphery of a thread-wound portion wound with the thread 107 to fix the thread-wound portion.

BRIEF SUMMARY OF THE INVENTION

According to a first aspect of the present invention, there is provided an endoscope including an insertion portion, a resin tubular covering member, a fastening member and a contact surface. The insertion portion includes a bending portion. The resin tubular covering member is covering a covering target part in the insertion portion including the bending portion. The fastening member is wound around the outer periphery of at least one end of the covering member and fastens the end to the covering target part. The contact surface is provided on the side of the covering target part covered with the end, is placed in contact with the end face of the covering member and becomes thinner toward the side of the covering member.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An endoscope 1 according to a preferred embodiment of the present invention will hereinafter be described with references to the drawings. The same reference numbers are assigned to elements having substantially the same configuration in the specification and the drawings, and redundant explanations are omitted.

Figure 1:
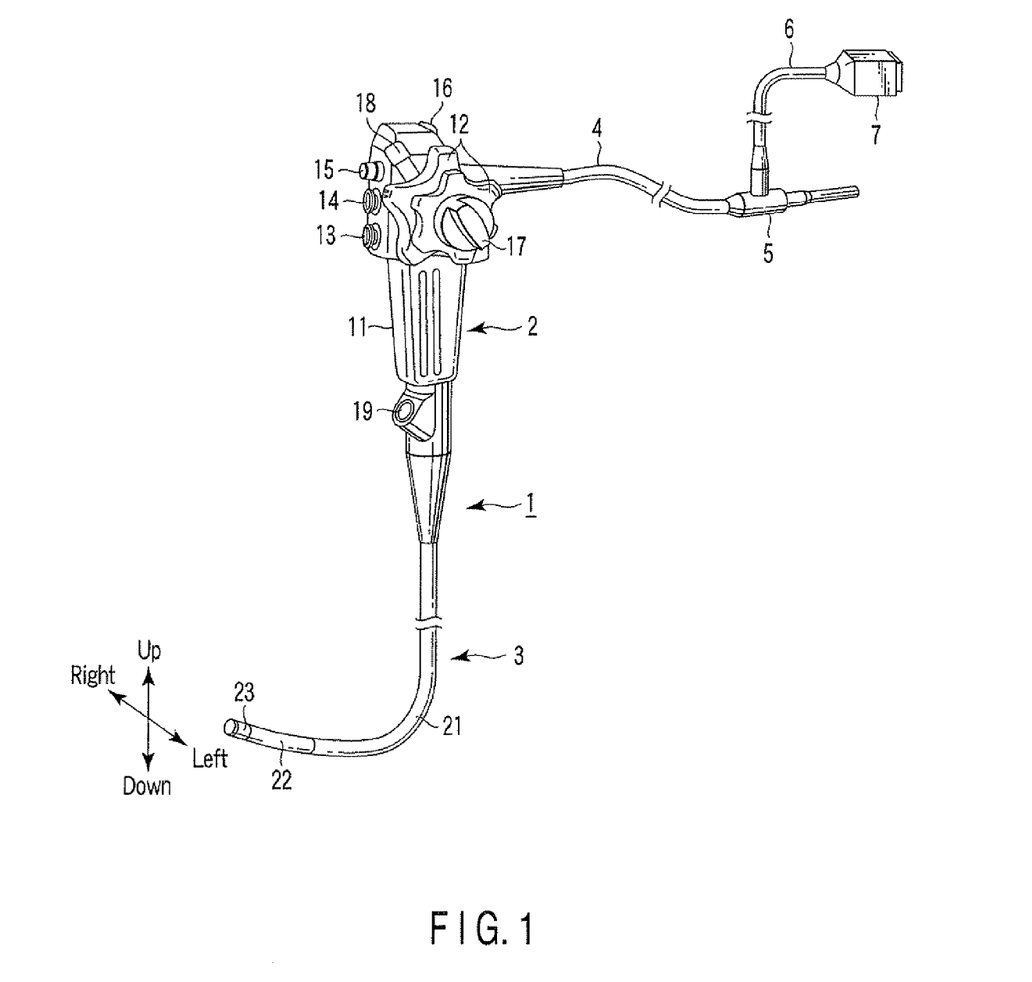
FIG. 1 is a schematic perspective view of an endoscope according to an embodiment of the present invention.

FIG. 1 is a perspective view schematically showing the whole endoscope 1. While the endoscope 1 is described here as an electronic type which picks up an image of the endoscope 1 by an image pickup portion 37 having an image pickup device as described later, an endoscope of, for example, a fiber type using an image guide fiber may be used instead.

As shown in FIG. 1, the endoscope 1 includes an operation portion 2, and an elongate insertion portion 3 to be inserted into a body cavity. A proximal end (rear end) of the insertion portion 3 is connected to the operation portion 2. The operation portion 2 is provided with a universal cord 4. A light guide connector 5 connectable to an unshown endoscopic light source unit is connected to an extended end of the universal cord 4. The light guide connector 5 is provided with a video cable 6. An extended end of the video cable 6 is provided with a video connector 7. The video connector 7 is connectable to an unshown video processor.

The operation portion 2 is provided with a grip portion 11, an angle operation knob 12, an air/water sending operation button 13, a suction operation button 14, a gas supply operation button 15, switches 16, an operation knob fixing knob 17, an operation knob fixing handle 18, etc. On a distal side with respect to the position of the grip portion 11 (on the side of the insertion portion 3), an insertion opening 19 for the insertion of, for example, an unshown treatment tool through an insertion channel is provided.

The insertion portion 3 includes a flexible tube (flexible portion) 21, a bending portion 22 connected to the distal end of the flexible tube 21, and a distal hard portion 23 connected to the distal end of the bending portion 22, in order from the side of the operation portion 2 (hand side (proximal side)) to the distal side with respect to the operation portion 2. Here, the flexible tube 21 has flexibility such that it shows cushiony elasticity and can bend when subjected to external force. In addition, a hard tube which does not bend even when subjected to external force that can be generated in the body cavity may be used instead of the flexible tube 21.

The bending portion 22 bends in four horizontal and vertical directions with respect to a substantially neutral state shown in FIG. 1 by turning the angle operation knob 12. Thus, the direction of the distal hard portion 23 can be changed by the bending of the bending portion 22.

Figure 2:
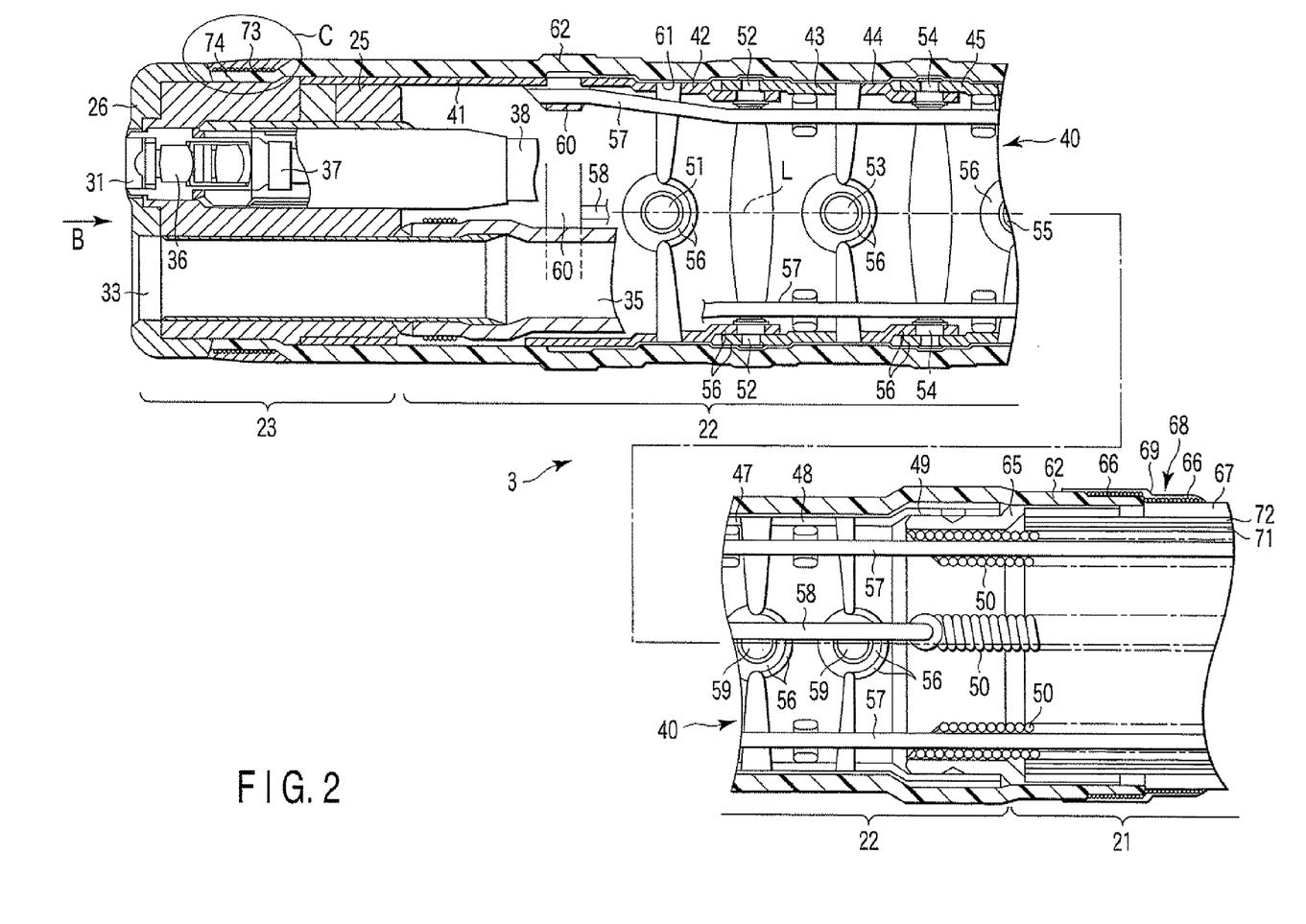
FIG. 2 is a schematic longitudinal sectional view along the A-O-A line shown in FIG. 3, showing a distal hard portion, a bending portion and the vicinity of a distal portion of a flexible tube of an insertion portion of the endoscope.
Figure 3:
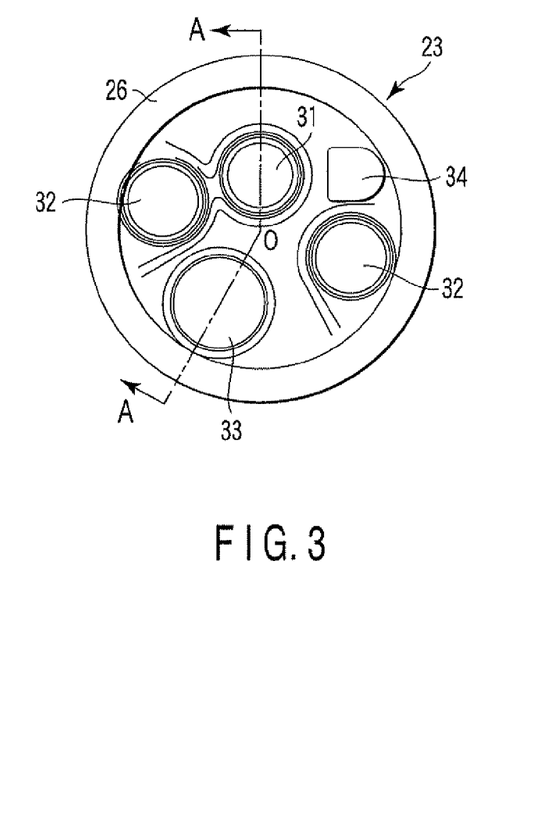
FIG. 3 is a front view of a distal portion of the insertion portion of the endoscope shown from the direction of an arrow B shown in FIG. 2.

As shown in FIG. 2, the distal hard portion 23 includes a hard distal hard portion main body (hereinafter mainly referred to as a main body) 25 made of, for example, a metal material, and a distal hard portion cover (hereinafter mainly referred to as a cover) 26 made of an insulating resin material. The cover 26 covers the outer surface of the main body 25 made of the metal material as, for example, a measure against electric leakage due to a high-frequency current. The cover 26 covers a distal end face at the distal portion of the main body 25, and the peripheral surface of the distal portion. The cover 26 is airtightly fixed to the main body 25. As shown in FIGS. 2 and 3, an observation window 31, illumination windows 32, a channel port 33 and a nozzle 34, etc, are provided in the distal end face portions of both the main body 25 and the cover 26 of the distal hard portion 23.

As shown in FIG. 2, an optical system 36 such as an objective lens, and the image pickup portion 37 equipped with the image pickup device such as a CCD or CMOS are provided inside the observation window 31. The image pickup portion 37 picks up an image of, for example, a lesion in the body cavity taken in through the optical system 36. An imaging signal obtained by the image pickup in the image pickup portion 37 is sent to the video processor connected to the video connector 7 of the video cable 6 through a signal line 38. The signal line 38 extends throughout and is disposed inside the insertion portion 3, the operation portion 2, the universal cord 4 and the video cable 6. Illumination light is supplied to the illumination windows 32 from the endoscopic light source unit through an unshown light guide which extends throughout and is disposed inside the insertion portion 3, the operation portion 2 and the universal cord 4. Thus, the illumination light is applied to, for example, the lesion in the body cavity through the illumination windows 32. The channel port 33 is connected to an insertion channel 35 disposed in the insertion portion 3. The hand side of the insertion channel 35 is connected to the insertion opening 19.

Next, the bending portion 22 is described. As shown in FIG. 2, the bending portion 22 includes a joint bending mechanism 40 including a plurality of bending pieces (joint pieces) 41, 42, . . . , 49. Each of the bending pieces 41, 42, . . . , 49 is formed of an annular member. The bending pieces 41, 42, . . . , 49 are coaxially aligned in a long axis direction (central axis) L of the insertion portion 3. Here, they are called the first bending piece 41, the second bending piece 42, . . . , the ninth bending piece 49 in order from the distal side to the proximal side. The first bending piece 41 and the second bending piece 42 are coupled together relatively turnably in a vertical direction shown in FIG. 1 when viewed from the proximal side (the side of the operation portion 2), by a first turning shaft 51 which has an axial center in a direction perpendicular to the central axis L of the insertion portion 3 and along a horizontal lateral direction (see FIG. 1). The second bending piece 42 and the third bending piece 43 are coupled together relatively turnably in a horizontal direction when viewed from the proximal side (the side of the operation portion 2), by a second turning shaft 52 which has an axial center in a direction perpendicular to the long axis direction L of the insertion portion 3 and along the vertical direction. The third bending piece 43 and the fourth bending piece 44 are coupled together relatively turnably in a vertical direction when viewed from the proximal side (the side of the operation portion 2), by a third turning shaft 53 which has an axial center in the direction perpendicular to the central axis L of the insertion portion 3 and along the horizontal lateral direction. In a similar manner, the following bending pieces are sequentially coupled together by joints configured by portions of turning shafts 54, 55 so that the directions of the turning shafts alternately shift 90°. Therefore, every other bending piece arranged in the joint bending mechanism 40 turns in the same direction. However, the seventh to ninth bending pieces 47, 48, 49 located on the rear side of the joint bending mechanism 40 are coupled together by a turning shaft 59 which has an axial center in the direction perpendicular to the central axis (long axis) L of the insertion portion 3 and along the horizontal lateral direction, so that the seventh to ninth bending pieces 47, 48, 49 can only turn in the vertical direction when viewed from the proximal side (the side of the operation portion 2). The ninth bending piece 49 at the terminal end of the joint bending mechanism 40 is connected to the distal end of the flexible tube 21 by a joint tube 65 described later.

As shown in FIG. 2, the first to ninth bending pieces 41, 42, . . . , 49 of the joint bending mechanism 40 have tongue-like coupling portions 56 projecting from their end edges. The respective turning shafts 51 to 59 are formed by rivet-shaped shaft members which overlap the coupling portions 56 of the first to ninth bending pieces 41, 42, . . . , 49 and which penetrate through the part where the coupling portions 56 overlap. The distal ends of four operation wires including a pair of operation wires 57 as a vertical set and a pair of operation wires 58 as a horizontal set are connected to the first bending piece 41 located at the distal most end.

Here, the right part (see FIG. 1) of the first bending piece 41 is defined by the right half of the first bending piece 41 which is divided into right and left parts by a plane through the central axis of the first bending piece 41 corresponding to the central axis L of the insertion portion 3 and through a line perpendicular to the turning central axis of the first turning shaft 51. The left part (see FIG. 1) thereof is likewise defined by the left half of the first bending piece 41 divided into right and left parts by the above-mentioned plane. The upper part (see FIG. 1) of the first bending piece 41 is defined by the upper half of the first bending piece 41 which is divided into upper and lower parts by a plane through the central axis of the first bending piece 41 and the central axis of the first turning shaft 51. The lower part (see FIG. 1) thereof is likewise defined by the lower half of the first bending piece 41 divided into upper and lower parts by the above-mentioned plane. Thus, the distal end of the upper operation wire 57 is connected to the upper part of the first bending piece 41, and the distal end of the lower operation wire 57 is connected to the lower part of the first bending piece 41. The distal end of the right operation wire 58 is connected to the right part of the first bending piece 41, and the distal end of the left operation wire 58 is connected to the left part of the first bending piece 41. In order to connect the operation wires 57, 58 to the first bending piece 41, the wall portion of the first bending piece 41 corresponding to the connection parts is inwardly cut off, and the distal ends of the operation wires 57, 58 are inserted into cutoff pieces 60 and fixed by, for example, soldering, as shown in FIG. 2.

The respective operation wires 57, 58 are formed by a non-stretchy material. The operation wires 57, 58 are guided up to the operation portion 2 through a wire guide sheath 50 disposed inside the insertion portion 3, and connected to a bending operation mechanism operated by the angle operation knob 12. Thus, the bending operation mechanism is driven by the angle operation knob 12 to draw in and out the operation wires 57, 58, such that the bending portion 22 bends in the direction in which the operation wires 57, 58 are pulled.

The outside of the first to ninth bending pieces 41 to 49 of the joint bending mechanism 40 of the bending portion 22 is covered with a braid tube 61 produced by interlacing or weaving strands made of a stainless steel material or aramid fiber strands into a tubular form (see FIG. 2). Both ends of the braid tube 61 are fixed by, for example, soldering to the outer periphery of the first bending piece 41 at the distal most end and to the outer periphery of the ninth bending piece 49 at the rearmost end. The outer periphery of the braid tube 61 is covered with a tubular flexible envelope (covering member) 62. The envelope 62 is formed of a resin material, for example, fluoro-rubber such as PTFE. Both ends of the envelope 62 extend to both the distal side and rear side beyond the range of the bending portion 22. The front end portion of the envelope 62 covers the outer periphery of the main body 25 of the distal hard portion 23. The rear end portion of the envelope 62 covers the outer periphery of the joint tube 65 (see FIG. 2). That is, parts targeted to be covered by the envelope 62 (covering target parts) are not limited to the members (e.g., the joint bending mechanism 40 (the bending pieces 41 to 49), the braid tube 61) constituting the bending portion 22.

The rear end portion of the envelope 62 covers the outer peripheral surface (covering target part) of the joint tube 65 for connecting the bending portion 22 to the flexible tube 21. A thread 66 as a fastening member is wound around the outer periphery of the rear end portion of the envelope 62, and fixes and fastens the envelope 62 to the joint tube 65, thus forming a thread-wound portion 68. The thread-wound portion 68 is intended to be wound together with the thread 66 for winding the distal portion of an envelope tube 67 of the flexible tube 21. The thread-wound portion 68 is fixed by the application of an adhesive 69. Here, there is a step portion in a part where the rear end of the envelope 62 on the side of the bending portion 22 is in collision with the distal end of the envelope tube 67 on the side of the flexible tube 21, so that a step corresponding to the height of the step portion emerges in the surface of the thread-wound portion 68. The envelope tube 67 of the flexible tube 21 covers the outer peripheries of the core members of a spiral tube 71 and a braid tube 72 of the flexible tube 21.

Figure 4:
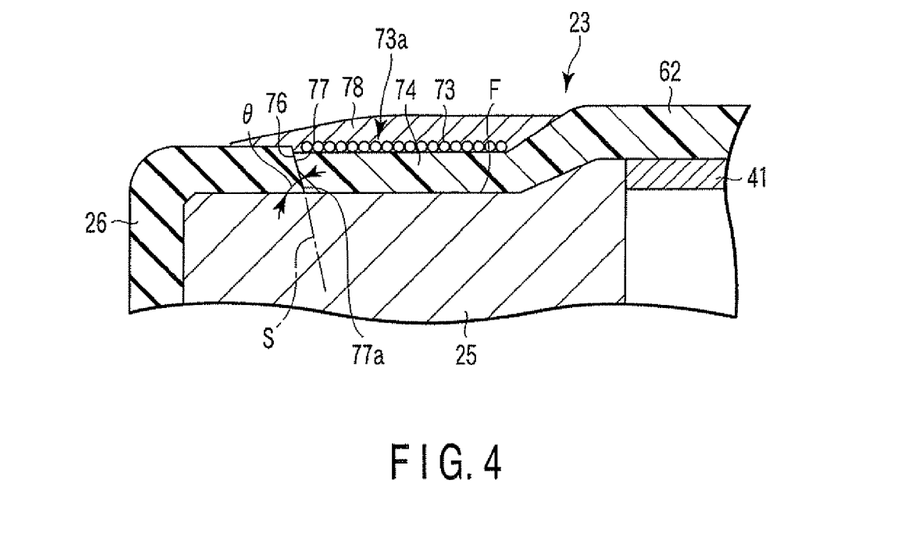
FIG. 4 is a sectional view in which a part indicated by a reference mark C in FIG. 2 is enlarged.

The distal end of the envelope 62 covering the outside of the bending portion 22 extends to the main body 25 of the distal hard portion 23 beyond the distal end of the braid tube 61 of the bending portion 22 and further beyond the first bending piece 41 to cover the outer peripheral surface (covering target part) of the main body 25, as shown in FIG. 2. For example, a thread 73 is wound as a fastening member on the outer periphery of a distal portion 74 of the envelope 62. The distal portion 74 of the envelope 62 is fastened and fixed to the outer periphery (covering target part) of the main body 25 by the thread 73. Therefore, as shown in FIG. 4, the thickness of the distal portion (thread-wound portion) 74 of the envelope 62 wound with the thread 73 is diametrically inwardly pressed by the fastening force of the thread 73, and thus becomes smaller than before fastening. In addition, the outside of a thread-wound portion 73a wound with the thread 73 is bonded and fixed by an adhesive 78.

Furthermore, the rear end face of the cover 26 located at the distal end of the envelope 62 forms a step having a height equal to the thickness of the cover 26. That is, a step is formed by the outer peripheral surface of the main body 25 and the rear end face of the cover 26. The step is formed over the whole circumference of the main body 25. Further, a distal end (cut inclined surface) 76 of the envelope 62 is placed in collision with the end face of the step (the rear end face of the cover 26). The height of the step (the thickness of the rear end face of the cover 26) preferably corresponds to the thickness of the envelope 62 when the thread 73 is wound. The height of the step here substantially corresponds to the addition of the thickness of the wound thread 73 to the height of the envelope 62.

Figure 5:
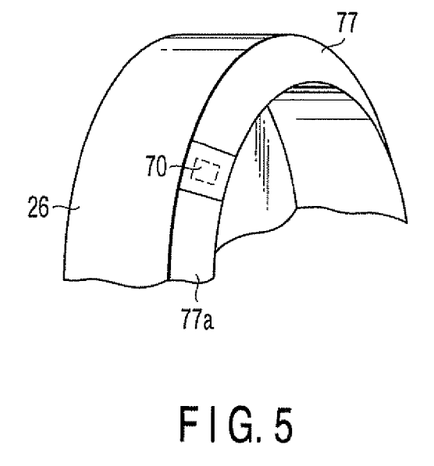
FIG. 5 is a schematic perspective view showing part of a cover of the distal hard portion.

Moreover, the end face of the step formed by the rear end face of the cover 26 is not a wall surface perpendicular to the outer peripheral surface (covering target part) of the main body 25 of the distal hard portion 23 covered with the end of the envelope 62, but is formed into an inclined surface 77a. Thus, the inclined surface 77a serves as a contact surface 77 with which the distal end face (distal end 76) of the envelope 62 is in contact. The inclined surface 77a (contact surface 77) here is formed as a tapered peripheral surface gradually reduced in diameter toward the proximal side of the envelope 62, as shown in FIGS. 4 and 5. In other words, the inclined surface 77a of the cover 26 linearly inclines and decreases in diameter, and what is called the taper angle or inclination angle of the inclined surface 77a is constant and unchanged.

As shown in FIG. 4, the inclined surface 77a of the cover 26 inclines toward the distal end of the cover 26 with reference to an outer peripheral surface F of the covering target part of the main body 25. That is, the inclined surface 77a is formed as a tapered peripheral surface greater in diameter on the distal side of the cover 26 and smaller in diameter on the proximal side of the envelope 62. Thus, as shown in FIG. 4, the longitudinal sectional shape of the contact surface 77 when the cover 26 is vertically sectionally viewed is observed as a straight line as indicated by a reference S. Further, an inclination angle θ of the straight line S with respect to the outer peripheral surface F of the main body 25 is in a range of more than 0° and less than 90°. The angle θ preferable in terms of the prevention of remaining air bubbles and operability in the range is 60° to 75°.

As shown in FIG. 5, a resin injection gate 70 used in molding the cover 26 with a resin is formed in the contact surface 77 formed by the rear end face of the cover 26. The resin injection gate 70 is processed to be flat (an inclined surface) along the inclined surface 77a (contact surface 77) of the rear end face, and therefore causes no trouble even if the distal end 76 of the envelope 62 is brought into collision.

Next, the operation of covering the bending portion 22 with the envelope 62 is described. The procedure of the operation is carried out in the same order as that shown in FIGS. 16A to 16D described above. First, as in FIG. 16A, the envelope 62 is placed to cover from the position of the bending portion 22 to the distal hard portion 23. The inside diameter of the envelope 62 in a free state is smaller than the outside diameter of the main body 25, so that the envelope 62 covers from the main body 25 to the cover 26 in a substantially close contact state.

Then, as in FIG. 163, the thread 73 is wound around the outer peripheral part of the envelope 62 in a predetermined range to form the thread-wound portion 73a. Then, as in FIG. 16C, the cutter 108 (e.g., a razor) is put on a portion extended and budged due to the step, and an extra portion of the distal side of the envelope 62 covering the cover 26 beyond the step is cut off. At this point, the cutter 108 is guided along the inclined surface 77a (contact surface 77) of the cover 26. Therefore, the distal end 76 of the envelope 62 is formed as a cut inclined surface which has been obliquely cut.

As shown in FIG. 16D, the distal portion 74 of the envelope 62 comes into the step formed by the contact surface 77 at the rear end of the cover 26 and the outer peripheral surface of the main body 25 owing to the elasticity possessed by the envelope 62 itself. At this point, the distal end (cut inclined surface) 76 of the envelope 62 contacts the inclined surface 77a of the contact surface 77. Finally, as shown in FIG. 4, the thread-wound portion 73a is fixed by applying the adhesive 78 to the outside of the thread-wound portion 73a in which the thread 73 is wound around the outer peripheral surface of the distal portion 74 of the envelope 62, such that watertightness is achieved between the distal end 76 of the envelope 62 and the inclined surface 77a of the contact surface 77.

In the step of covering with the envelope 62 as described above, the distal end 76 of the envelope 62 comes into the step formed by the rear end of the cover 26 and the outer peripheral surface of the main body 25 when the extra distal portion of the envelope 62 is cut off by the cutter 108. Thus, the distal end 76 of the envelope 62 contacts the contact surface 77. Since the inclined surface 77a is formed in the contact surface 77, the distal end (cut inclined surface) 76 of the envelope 62 comes in close contact with the contact surface 77 in such a manner as to push the air inside the envelope 62 out of the envelope 62 when the distal portion (projecting portion) 74 of the envelope 62 comes into the step. A gap, if any, is significantly small which tends to be generated at the same time due to the inclination of the inclined surface 77a of the contact surface 77 between the distal end 76 of the envelope 62 and the contact surface 77 in contact with the distal end 76. Thus, there is only a slight amount of remaining air (the volume of air).

Figure 6:
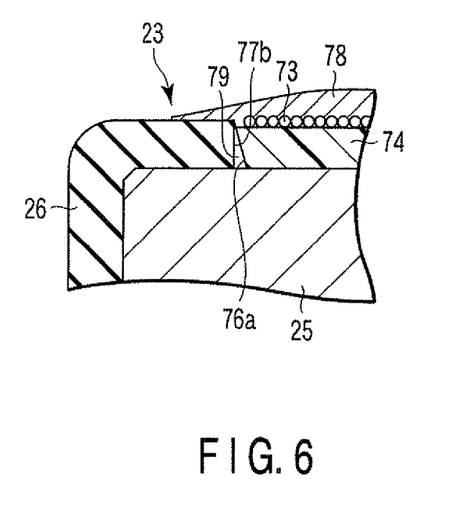
FIG. 6 is a schematic longitudinal sectional view showing part of a distal hard portion of an insertion portion of an endoscope according to a prior art.

In the meantime, as shown in FIG. 6 concerning a prior art, the presence of a wedge-shaped gap 79 which tends to be generated between a distal end 76a of the envelope 62 and a contact surface 77b of the cover 26 which is not an inclined surface is often not so sized as to be visible to the naked eye, and it may be difficult to judge by visual observation whether the gap 79 is present. Such a gap 79 is inevitable even if the operation of winding the thread 73 around the envelope 62 and the operation of cutting off the extra portion of the distal side of the envelope 62 by the cutter are carefully done. Thus, it is difficult in the prior art to effectively prevent the production of a defective product in which air bubbles seeping out of the border between the contact surface 77b of the cover 26 and the distal end 76a of the envelope 62 are observed after the fact.

On the contrary, in this embodiment, the contact surface 77 is formed as the inclined surface 77a as shown in FIG. 4, and the cut inclined surface 76 formed by cutting the envelope 62 is brought into contact with the inclined surface 77a, such that it is possible to inhibit the wedge-shaped gap 79 from being formed by the inclined surface 77a and the cut inclined surface 76, enhance the close contact between the distal end 76 of the envelope 62 and the contact surface 77, and hold down the amount (volume) of generated gap 79.

Figure 15B:
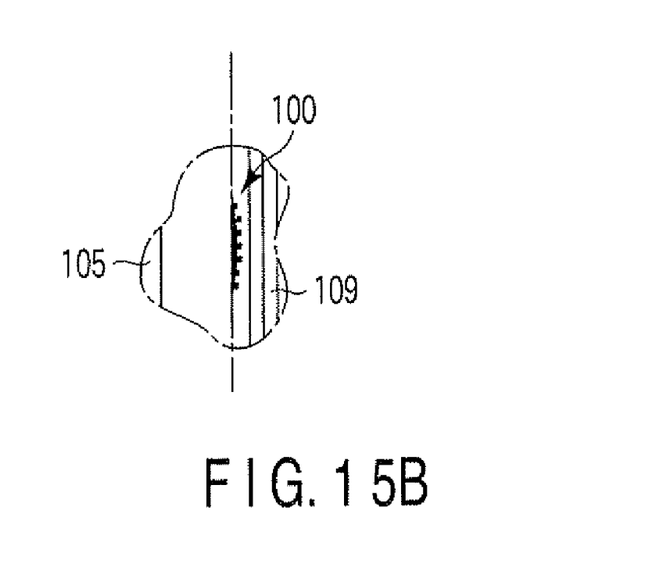
FIG. 15B is a schematic plan view in which the border between a cover of the distal hard portion and an envelope which covers a bending portion is viewed through an adhesive from the direction of an arrow H shown in FIG. 15A, in the outer periphery of the distal hard portion of the insertion portion of the endoscope according to the prior art.

Therefore, it is possible to significantly reduce the occurrence of a phenomenon which cannot be recognized until the drying step after the application of the adhesive 78 to the outer periphery of the thread-wound portion 73a wherein air bubbles 100 and their shadows appear as shown in FIG. 15B outside the main body 25 of the distal hard portion 23 and in the vicinity of the border between the rear end of the cover 26 and the distal end 76 of the envelope 62. The operation of winding the thread 73 around the outer peripheral surface of the distal portion 74 of the envelope 62 and the operation of cutting off the extra distal portion of the envelope 62 by the cutter 108 are facilitated, and there is less production of defective products, so that manufacturing costs can be significantly reduced.

According to the present embodiment, the inclined surface 77a is formed in the contact surface 77 of the step with which the end face (distal end) 76 of the covering member (envelope) 62 is in contact, and the rear end face of the cover 26 of the distal hard portion 23 is formed to fill the gap 79 (see FIG. 6) which tends to be generated between the contact surface 77 and the end face 76 of the covering member 62, such that it is possible to prevent the production of air bubbles which tend to remain in the gap 79 and increase the performance of the close contact between the end face 76 of the covering member 62 and the contact surface 77. Thus, it is possible to reduce the air remaining between the end face 76 of the covering member 62 and the contact surface 77. This allows the reduction of the production of defective products in which air bubbles and their shadows appear. Moreover, difficulty is reduced in the operation of winding, for example, the thread 73 around the envelope 62 and in the operation of cutting off the extra distal portion of the envelope 62 by the cutter, so that the operations are facilitated. Thus, in the endoscope 1 having such a structure, it is possible to prevent the production of defective products and reduce the manufacturing costs.

While the contact surface 77 formed by the end face of the step at the rear end of the cover 26 is formed into the tapered inclined surface 77a which linearly decreases in diameter as the distance from the distal end of the cover 26 increases in the example described above, the contact surface 77 is not limited to the inclined surface 77a and may be in the shapes respectively shown in FIGS. 7A to 11.

Figure 7A:
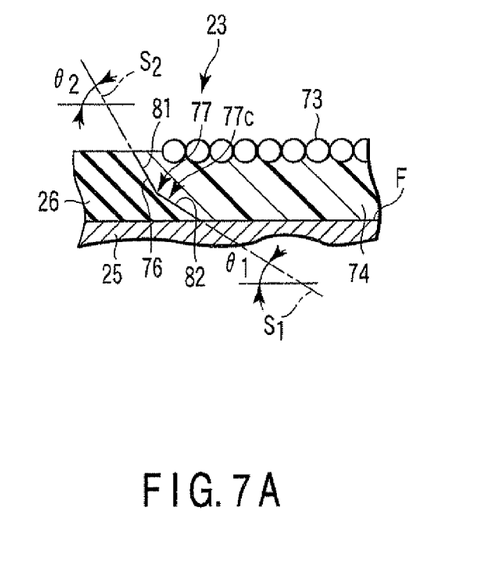
FIG. 7A is a sectional view showing another example in which the part indicated by the reference mark C in FIG. 2 is enlarged.
Figure 7B:
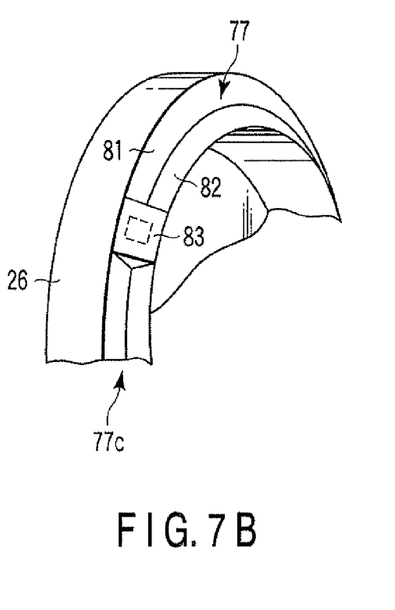
FIG. 7B is a schematic perspective view showing another example of part of the cover of the distal hard portion.

In the example shown in FIGS. 7A and 7B, the longitudinal sectional shape of the contact surface 77 when the cover 26 is longitudinally sectioned is a concave inclined surface 77c which bends halfway. That is, the contact surface 77 has the inclined surface 77c having two tapered inclined surface portions 81, 82 with different angles.

Here, an inclination angle made by a straight line S1 indicated by the longitudinal sectional shape of the inner (on the side of the main body 25) inclined surface portion 81 of the concave inclined surface 77c is θ1, an inclination angle made by a straight line S2 indicated by the longitudinal sectional shape of the outer inclined surface portion 82 is θ2. The inclination angle θ1 of the inner inclined surface portion 81 is smaller than the inclination angle θ2 of the outer inclined surface portion 82. Therefore, the inner inclined surface portion 81 can strongly inhibit the generation of the above-mentioned gap 79 (see FIG. 6), and the outer inclined surface portion 82 can contribute to guiding and positioning functions when the distal portion 74 of the envelope 62 comes into the step between the contact surface 77 of the cover 26 and the outer peripheral surface of the main body 25.

In addition, in this case as well, a resin injection gate (gate processing portion) 83 used in molding the cover 26 with a resin is formed in the contact surface 77, and the step remains partly between the inclined surface portions 81, 82 and the gate 83 as shown in FIG. 7B. The presence of the gate 83 is not as significant as to prevent the inner inclined surface portion 81 from strongly inhibiting the generation of in the gap 79 (see FIG. 6) and prevent the outer inclined surface portion 82 from contributing to the guiding and positioning functions when the distal is portion 74 of the envelope 62 comes into the step between the contact surface 77 of the cover 26 and the outer peripheral surface of the main body 25.

Figure 8A:
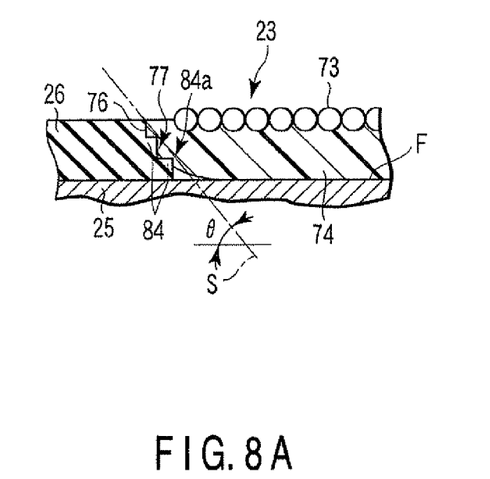
FIG. 8A is a sectional view showing another example in which the part indicated by the reference mark C in FIG. 2 is enlarged.
Figure 8B:
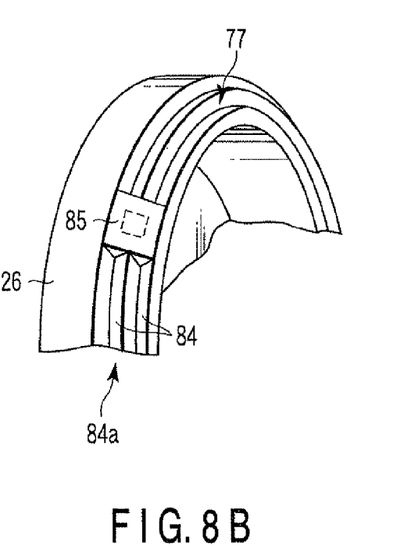
FIG. 8B is a schematic perspective view showing another example of part of the cover of the distal hard portion.

In the example shown in FIGS. 8A and 8B, a plurality of step portions 84 are provided in the contact surface 77 along the direction of the inclined surface. That is, the contact surface 77 when the cover 26 is longitudinally sectioned has a stair-like inclined surface 84a. The inclination angle θ of the inclined surface 84a in this case can be measured by, for example, the straight line S passing the apexes of the respective step portions 84 or the centers of the respective step portions 84 (the apexes in FIG. 8A). The respective step portions 84 are formed on the whole circumference of the outer peripheral surface of the cover 26.

Thus, by providing the step portions 84 in the contact surface 77 instead of the inclined surface 77a, the contact surface 77 is also formed so that it becomes gradually thinner from the distal end of the cover 26 to the proximal side of the envelope 62.

Furthermore, since the contact surface 77 is formed into a stair-like shape, the distal end 76 of the covering member 62 is held so that it does not easily dig into the step portions 84. Therefore, even if a slight amount of air bubbles remains inside the covering member 62, a function to confine the slight amount of air bubbles is generated, which can inhibit the after-the-fact seepage of the air bubbles.

In addition, in this case as well, a resin injection gate (gate processing portion) 85 used in molding the cover 26 with a resin is formed in the contact surface 77, and the step remains partly between the step portions 84 and a gate 85 as shown in FIG. 8B. The presence of the gate 85 is not as significant as to prevent the step portions 84 as the inclined surface 84a from strongly inhibiting the generation of the gap 79 (see FIG. 6) and from contributing to the guiding and positioning functions when the distal portion 74 of the envelope 62 comes into the step between the contact surface 77 of the cover 26 and the outer peripheral surface of the main body 25. In the meantime, increasing the number of the step portions 84 makes it closer to the example of the above-mentioned flat inclined surface 77a (see FIGS. 4 and 5).

Figure 9:
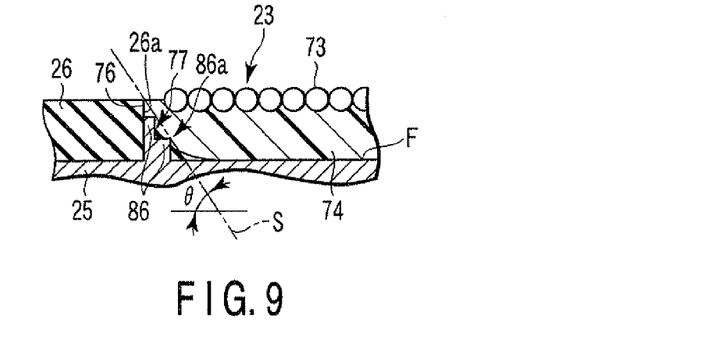
FIG. 9 is sectional views showing another example in which the part indicated by the reference mark C in FIG. 2 is enlarged.

In the example of the inclined surface shown in FIG. 9, the above-mentioned step portions 84 formed into the stair-like shape (see FIGS. 8A and 8B) are formed integrally with the main body 25 as indicated by a reference number 86. That is, the contact surface 77 is formed into the step portions 86 of the main body 25. In addition, a reference number 26a is assigned to a contact surface at the rear end of the cover 26 in contact with the front surfaces of the step portions 86. The contact surface 26a is formed as, for example, a surface orthogonal to the central axis L.

Since the portions (step portions 86) formed into the stair-like shape can be formed integrally with the metal main body 25, even an inclined surface 86a in a complex stair-like shape can be easily processed. Moreover, there is no longer a need to form the resin injection gate in the stair-like portions.

Figure 10:
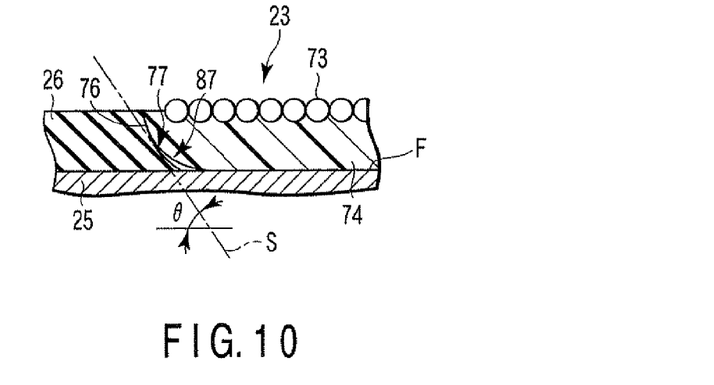
FIG. 10 is sectional views showing another example in which the part indicated by the reference mark C in FIG. 2 is enlarged.

In the example of an inclined surface 87 shown in FIG. 10, the longitudinal sectional shape of the contact surface 77 when the cover 26 is longitudinally sectioned is formed into a substantially arc-like concave shape. The inclination angle θ in this case can be measured by, for example, the straight line S tangent to the center of concave arc which emerges in the longitudinal section shown in FIG. 10. In this example, the distal portion 74 of the envelope 62 can be smoothly guided to the bottom (the outer peripheral surface of the main body 25 of the distal hard portion 23) in the step along the substantially arc-shaped concave inclined surface 87, so that the ability to discharge the air bubbles can be increased. Further, since the inclined surface 87 comes deep into the inner part of the distal portion 74 of the envelope 62, the gap which confines the air bubbles can be further reduced. Thus, the air remaining inside the envelope 62 can be further reduced.

Figure 11:
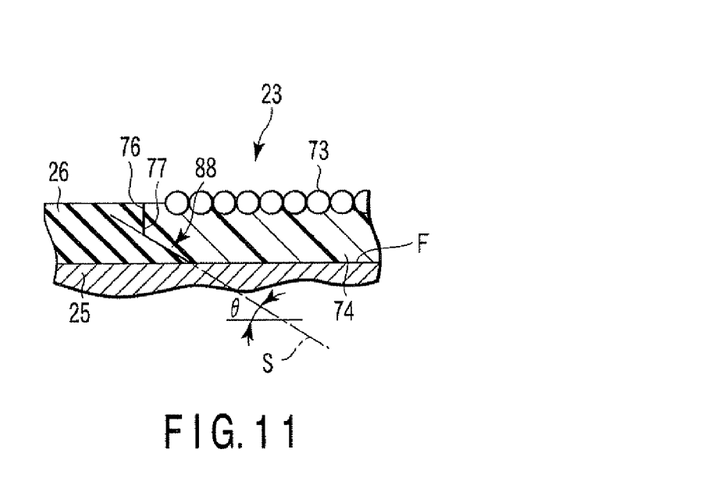
FIG. 11 is sectional views showing another example in which the part indicated by the reference mark C in FIG. 2 is enlarged.

In the example of an inclined surface 88 shown in FIG. 11, the whole contact surface 77 is not formed into the inclined surface 77*a* (see FIG. 4), and the inclined surface 88 is only formed in a part of a bottom side region in the end face of the step (part proximate to the outer peripheral surface of the main body 25). The examples shown in FIGS. 8A and 9 can be regarded as examples of this form. Further, the inclined surface 88 in the case shown in FIG. 11 is formed inside the contact surface 77 as a tapered peripheral surface which becomes gradually thinner toward the side of the envelope 62, and the inclined surface 88 fills the gap in the inner part of the step, which can particularly prevent the remaining of air bubbles. The ability to remove the air bubbles is thus enhanced, and the gap which confines the air bubbles is further reduced, so that the remaining of air bubbles can be further reduced.

In addition, the inclined surface forming the contact surface 77 may be in other forms such as a stepped shape, a curved-surface shape or a combination of these as long as it functions as an inclined surface as a whole. Moreover, the contact surface 77 is not exclusively formed by use of the cover 26, and may be formed integrally with the metal main body 25 as shown in FIGS. 12A to 12D. In the example shown in FIGS. 12A to 12D, the contact surface 77 is formed in the main body 25 in addition to the outer peripheral surface.

Figure 12A:
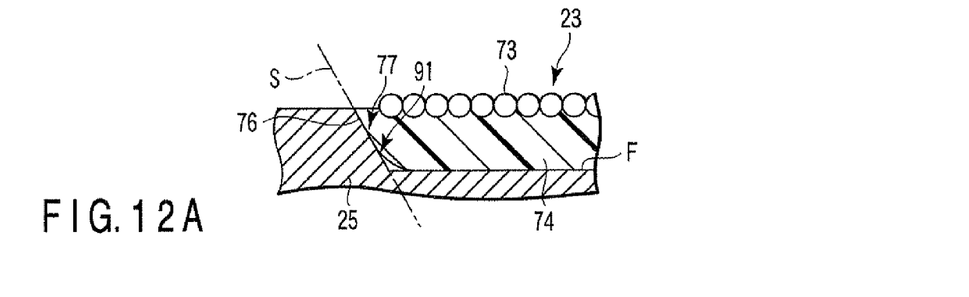
FIGS. 12A to 12D are sectional views showing another example in which the part indicated by the reference mark C in FIG. 2 is enlarged.

Thus, as shown in FIG. 12R, a step is formed by the outer peripheral surface and the contact surface 77 of the main body 25. The contact surface 77 has an inclined surface 91 whose longitudinal sectional shape is the straight line S to correspond to FIG. 4.

Figure 12B:
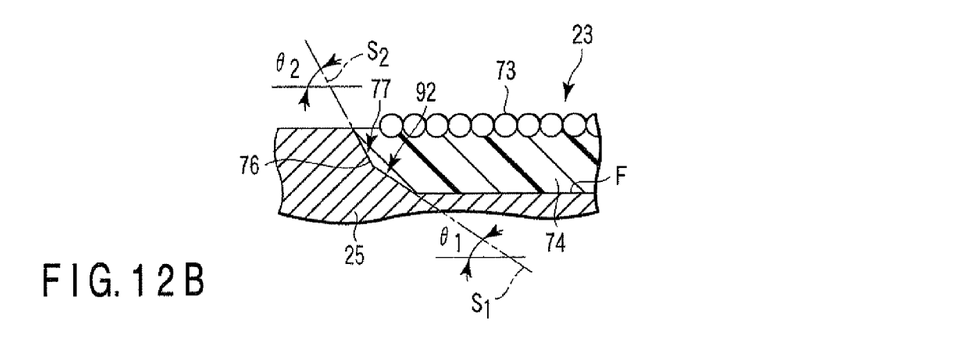

As shown in FIG. 12B, the contact surface 77 formed in the main body 25 has a concave inclined surface 92 whose longitudinal sectional shape bends halfway to correspond to FIG. 7A.

Figure 12C:
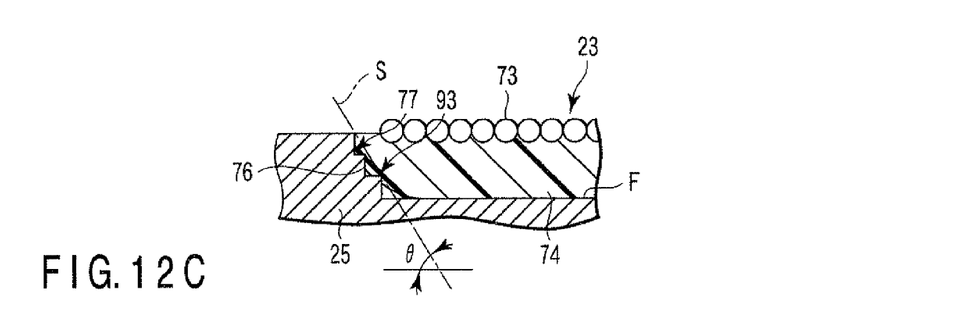

As shown in FIG. 12C, the contact surface 77 formed in the main body 25 has an inclined surface 93 formed into a stair-like shape to correspond to FIGS. 8A and 9.

Figure 12D:
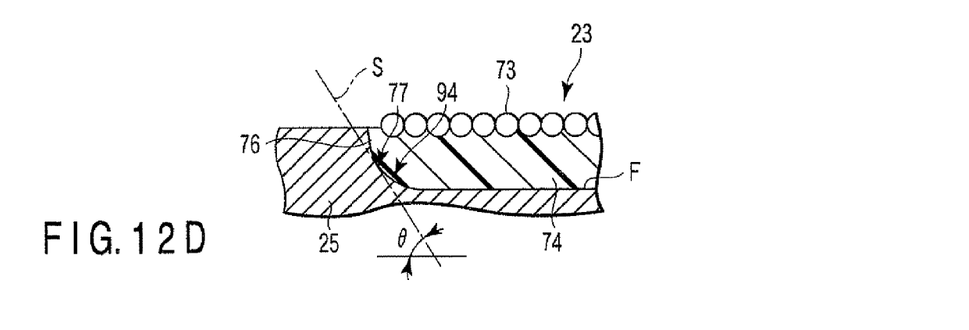

As shown in FIG. 12D, the contact surface 77 formed in the main body 25 has a substantially arc-shaped concave inclined surface 94 to correspond to FIG. 10.

As shown in FIGS. 12A to 12D, if the inclined surfaces 91, 92, 93, 94 are formed integrally with the metal main body 25, the inclined surfaces 91, 92, 93, 94 can be easily processed, and processing accuracy can be increased with low costs. Moreover, no resin injection gates have to be formed in the inclined surfaces 91, 92, 93, 94, and there is thus no need for gate processing.

Figure 13A:
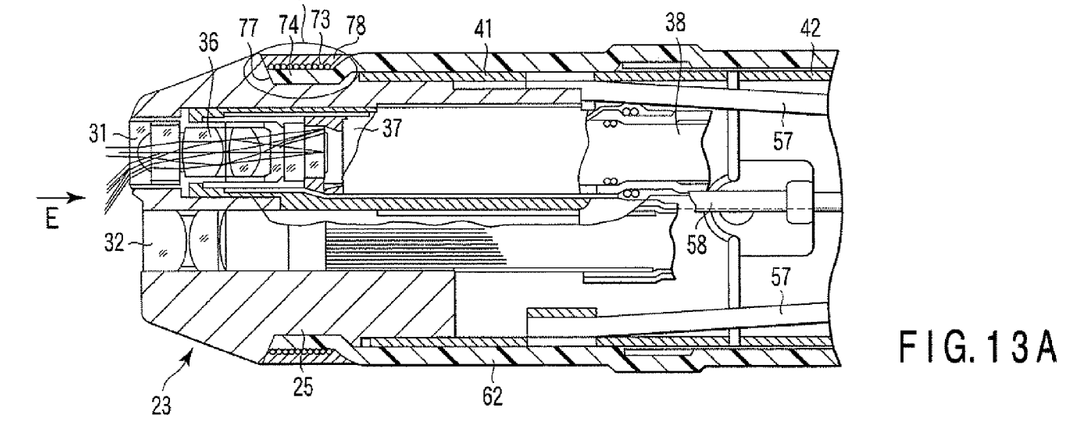
FIG. 13A is a schematic longitudinal sectional view along the D-O-D line shown in FIG. 13B, showing the vicinity of the distal portion of an insertion portion of a direct-view endoscope.
Figures 13B, 13C:
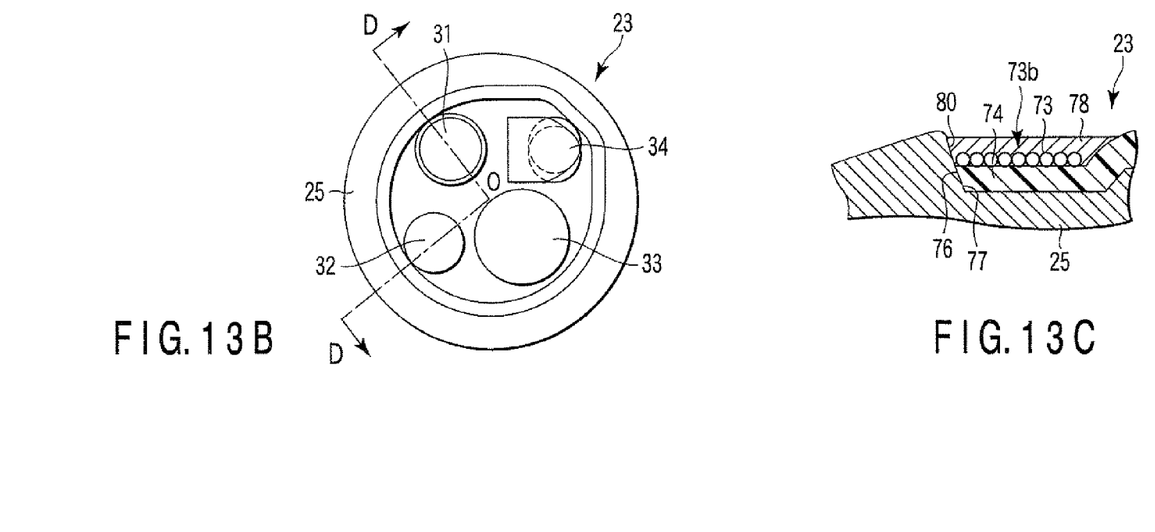
FIG. 13B is a front view of the distal portion of the insertion portion of the endoscope shown from the direction of an arrow E shown in FIG. 13A.
FIG. 13C is a schematic longitudinal sectional view showing a part indicated by a reference mark F in FIG. 13A in an enlarged manner.

FIGS. 13A to 13C show a direct-view endoscope which is not provided with any distal end cover. FIG. 13A shows a longitudinal sectional view of the distal hard portion 23, FIG. 13B shows a front view of the distal hard portion 23, and FIG. 13C shows an enlarged longitudinal sectional view of essential parts.

In this example, the cover 26 (see FIGS. 2 to 11) is not provided, so that the contact surface 77 with which the distal end face of the envelope 62 is to be in collision is directly formed on the outer periphery of the main body 25. Moreover, here, as shown in FIG. 13C, an inclined surface (extended inclined surface portion) 80 of the contact surface 77 is formed to extend further outward than the outer periphery of the distal portion 74 of the envelope 62 pressed inward by the fastening force of the thread 73. That is, in the outer peripheral surface of the main body 25 of the distal hard portion, the extended inclined surface portion 80 is formed which is an inclined surface extending further outward than the outer periphery of the distal portion 74 of the envelope 62 wound with the thread 73. Further, the extended inclined surface portion 80 is formed as mentioned above, so that when the extra end of the envelope 62 is cut after the outer peripheral surface of the distal portion 74 of the envelope 62 has been fastened by the thread to the main body 25 of the distal hard portion, the extended inclined surface portion 80 ensures that the distal end (cut surface) 76 of the envelope 62 is smoothly guided to the original colliding position of the extended inclined surface portion 80 and the distal portion 74 of the envelope 62 can be disposed at a predetermined position. Further, a concave portion for filling the adhesive 78 can be formed between the extended inclined surface portion 80 and the outer peripheral surface of the envelope 62, and the strength of securing a thread-wound portion 73*b* by the adhesive 78 can be increased.

Figure 14A:
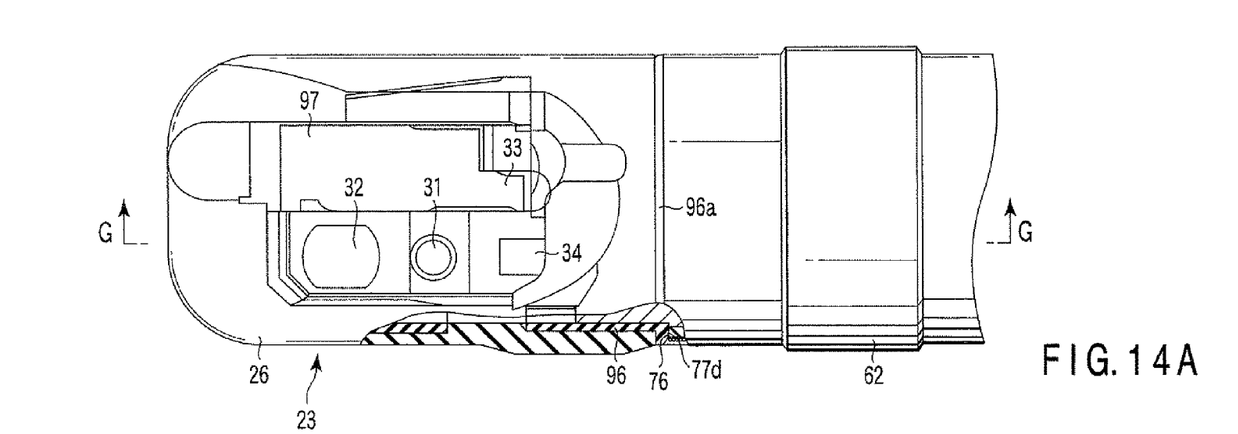
FIG. 14A is a plan view showing the vicinity of the distal portion of an insertion portion of a side-view endoscope.
Figure 14B:
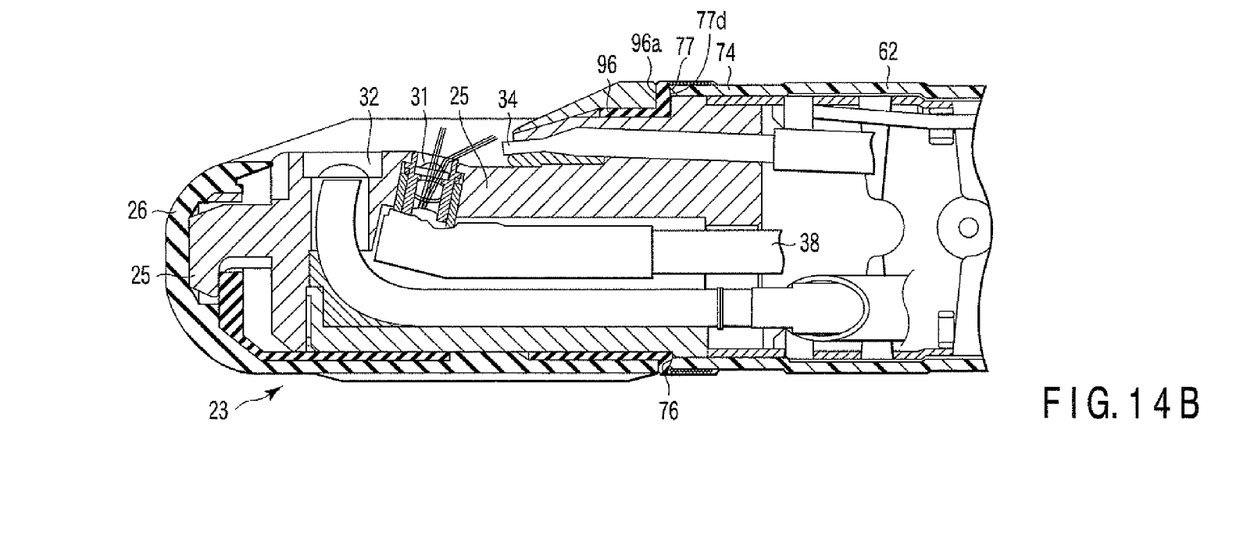
FIG. 14B is a schematic longitudinal sectional view along the G-G line in FIG. 14A.

FIGS. 14A and 14B show an example of a side-view endoscope in which the contact surface 77 having an inclined surface 77*d* is provided in a member which is neither the main body 25 nor the cover 26. FIG. 14A shows a plan view of the distal hard portion 23, and FIG. 14B shows a longitudinal sectional view of the distal hard portion 23.

Here, a fixing ring (adapter) 96 for supporting the cover 26 of the distal hard portion 23 is fixed to cover the main body 25. Further, the inclined surface 77*d* of the contact surface 77 with which the distal end face of the distal end 76 of the envelope 62 is to be in collision is formed in the fixing ring 96. An annular flange portion 96*a* standing diametrically outwardly along the rear end face of the cover 26 is formed at the rear end of the fixing ring 96. That is, the fixing ring 96 is disposed between the main body 25 and the cover 26.

Furthermore, the inclined surface 77*d* of the contact surface 77 is formed by the rear end face of the annular flange portion 96*a* of the fixing ring 96. Thus, the contact surface 77 is not formed in the main body 25 and the cover 26, that is, the contact surface 77 is formed in the member which is neither the main body 25 nor the cover 26, such that the contact surface 77 is easily formed and the side-view endoscope can be inexpensively manufactured.

In addition, here, the observation window 31 and the illumination window 32 are arranged at front and rear positions in the direction of the long axis L, and the channel port 33 equipped with a standing table 97 is disposed beside the observation window 31 and the illumination window 32.

Still further, the contact surface 77 is preferably formed in the same manner as the contact surface 77 shown in FIGS. 4 to 11.

Further yet, while the envelope 62 is fixed to the distal hard portion 23 in the cases mainly described here, the present invention is also applicable to the case where the envelope 62 is fixed to the joint tube (covering target part) 65 or the flexible tube (covering target part) 21. For example, when the rear end portion of the envelope 62 is fastened and fixed by a fastening member such as a thread, a step where the contact surface with which the rear end of the envelope 62 is put in contact may be formed in the covering target part in which the rear end portion of the envelope 62 is fitted, and a tapered inclined surface which becomes thinner toward the side of the envelope may be formed in the contact surface. That is, a similar contact surface 77 to contact the rear end portion of the envelope 62 may be formed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion portion including a bending portion, a distal hard portion provided at the distal end of the bending portion and including a main body;
   a resin tubular covering member covering a covering target part in the insertion portion including the bending portion, the covering member including a first end and a second end each having an end face;
   a fastening member which is wound around the outer periphery of at least the first end of the covering member and which fastens the first end to the covering target part;
   an insulating cover covering the distal side of the main body of the insertion portion; and
   a contact surface which is formed at the rear end of the insulating cover, and which is placed in contact with the end face of the first end of the covering member,
   wherein the contact surface of the insulating cover and the end face of the first end of the covering member include tapered inclined surface portions with a given inclination angle which are inclined with respect to a plane perpendicular to an outer peripheral surface of the covering target part, and the inclined surface portions come into contact with each other.

* * * * *